United States Patent [19]
Guibert et al.

[11] Patent Number: 5,755,412
[45] Date of Patent: May 26, 1998

[54] ADJUSTABLE STAND FOR HEAT APPLICATION

[76] Inventors: Raul Guibert; Bettina Guibert, both of 750 S. Bundy Dr., Brentwood, Calif. 90049

[21] Appl. No.: 801,632

[22] Filed: Feb. 18, 1997

[51] Int. Cl.$^6$ ........................................ A47F 5/00
[52] U.S. Cl. ........................ 248/122.1; 248/274.1; 403/384; 403/400; 403/403
[58] Field of Search ................ 248/122.1, 123.11, 248/123.2, 274.1, 280.1; 403/109, 372, 258, 403, 205, 382, 400, 384, 389, 396

[56] References Cited

U.S. PATENT DOCUMENTS

| | | | |
|---|---|---|---|
| 2,151,877 | 3/1939 | Walker | 248/123.2 |
| 4,548,373 | 10/1985 | Komura | 248/122 |
| 4,898,416 | 2/1990 | Hubbard et al. | 294/119 |
| 5,288,043 | 2/1994 | Tigliev | 248/123.1 |
| 5,331,181 | 7/1994 | Schweizer | 248/123.11 |

*Primary Examiner*—Ramon O. Ramirez
*Assistant Examiner*—Tan Le
*Attorney, Agent, or Firm*—Michael Ebert

[57] ABSTRACT

An adjustable stand anchored on a base to support an electrically-powered applicator so that it may be brought by an operator to a properly oriented position adjacent a selected site on the body of a subject to be treated and maintained at its set position. The stand is composed of series of interconnected arms, at least two adjacent arms being formed by pipes having a right angle bend and articulated by a knuckle formed by a four-sided rectangular block. The block has a first bore extending between one pair of opposing sides and a second bore extending between the other pair, an end of one arm being socketed in the first bore and the adjacent end of the other arm being socketed in the second bore whereby the arms articulated by the knuckle are swingable about axes at right angles to each other to afford a wide range of angular adjustment. Extending from each bore to a related side of the block is a slot which together with the bore and a set screw bridging the slot define an adjustable friction clutch that engages the arm socketed in the bore to maintain its angular position.

10 Claims, 2 Drawing Sheets

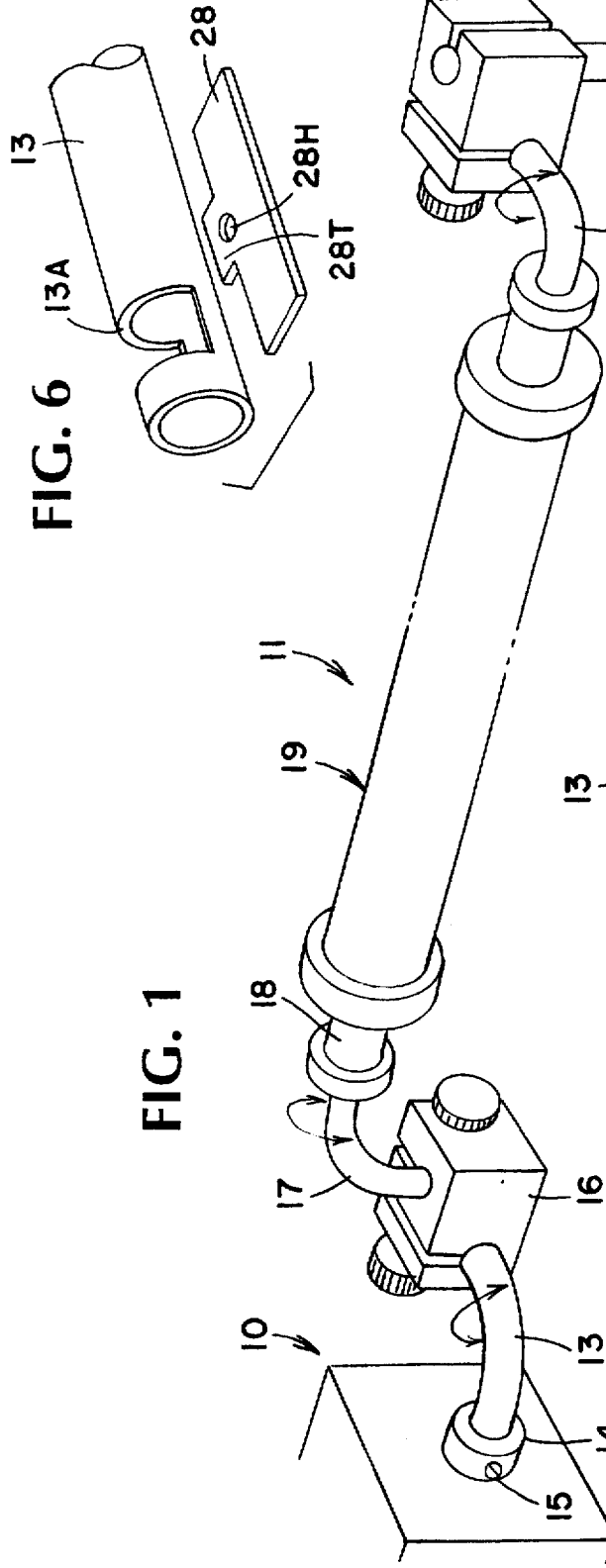
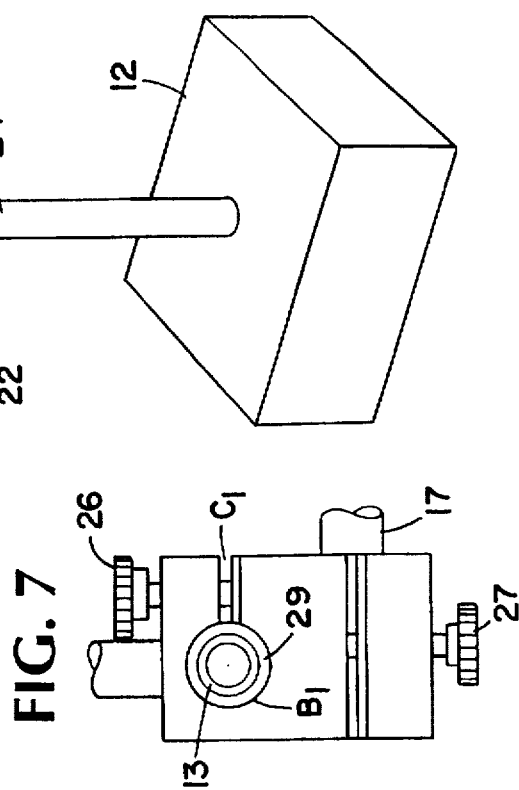
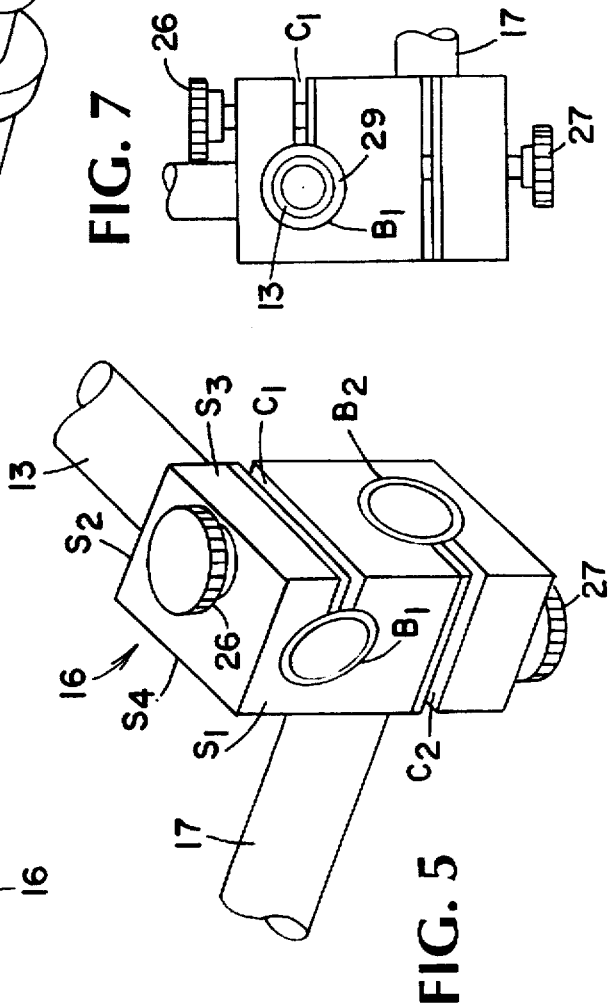

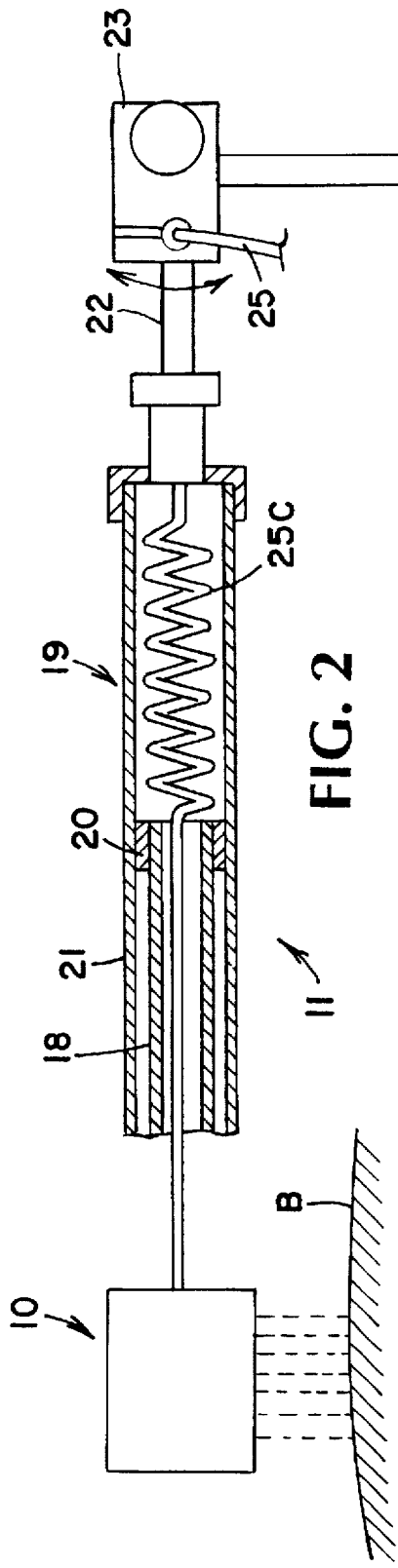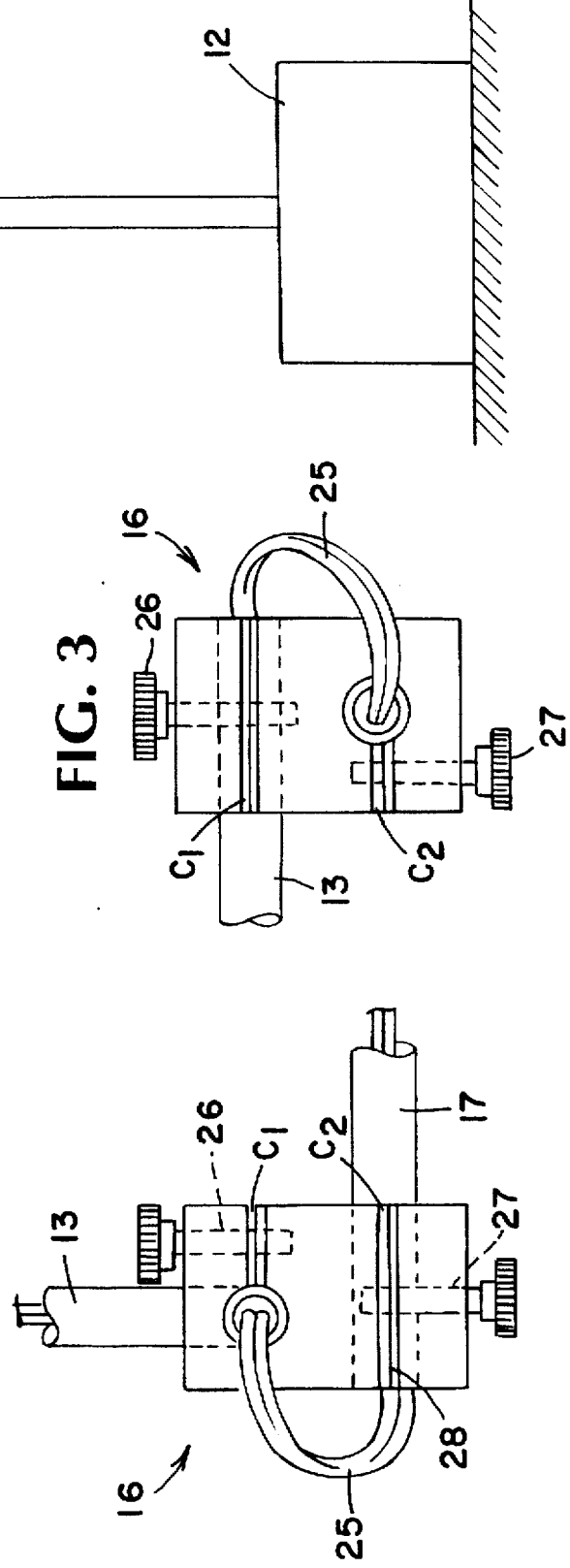

ADJUSTABLE STAND FOR HEAT APPLICATION

BACKGROUND OF INVENTION

1. Field of Invention

This invention relates generally to adjustable stands to support electrically-powered devices, and more particularly to a stand supporting a therapeutic heat applicator so that it can be properly oriented and placed adjacent a selected body site on a subject being treated by heat emanating from the applicator and maintained at this set position.

2. Status of Prior Art

In a goose-neck lamp, the reflector housing the bulb is supported by a flexible tube on a base, the cable supplying electric power to the bulb running through the tube. In a goose-neck lamp, the user can curve the tube so as to place the reflector at a position directing light rays from the bulb toward a desired site. The drawback of a goose-neck lamp is that unless the flexible tube is relatively short, it is incapable of maintaining an adjusted position. And a goose-neck tube cannot support a heavy reflector or lamp shade at an adjusted position, for the weight then at the end of the tube will cause it to bend.

Another well-known form of disk lamp, popularly referred to as LUXO lamp, makes use of an adjustable stand in the form of spring-biased articulated arms which extend between a weighted base and a reflector housing a light bulb. With a stand of this type one can lengthen or shorten the distance between the base and the reflector and thereby raise or lower the reflector. And one can also change the orientation of the reflector relative to the base so as to cause the reflector to assume a desired position. But the range of adjustment is limited by the fact that the articulated arms lie in a common plane.

Our prior U.S. Pat. No. 5,107,832 (Guibert) entitled "Universal Thermotherapy Technique" discloses a pulsed-heat applicator provided with a dome in which a motor-driven fan and a heater ring formed by a resistance coil. When the ring and the fan motor are energized, air blown by the fan through the coil is raised in temperature to a level that is a function of fan velocity, the higher the velocity the lower the temperature of the air.

The fan motor is controlled by an electronic unit which acts to periodically change the fan velocity to create high-temperature pulses which are applied therapeutically to a selected site on the body of the subject being treated.

In order to treat different sites on the body, such as on the shoulders or on the knees, the stand on which the pulsed-heat applicator is supported must be capable of adjustment to permit the applicator to reach the selected site and to be properly oriented with respect to this site.

While the prior Guibert patent discloses for this purpose a stand having pivoted arms and a universal joint, these expedients are inadequate when the site to be treated is relatively remote from the base of the stand.

Thus in some instance the site to be treated is fairly close to the base of the stand and is at a higher level, while in others the site is more distant from the base and at a lower level with respect thereto. And while a conventional adjustable stand, such as the type used to support a lamp may be capable of placing a heat applicator adjacent a body site to be treated that is remote from the base of the stand, it is not capable of maintaining the set position of the applicator.

The reason it is difficult for an adjustable stand anchored on a base and supporting a therapeutic heat applicator to maintain the applicator at a set position adjacent a body site to be treated is because the applicator is subjected to a moment of force or torque. The magnitude of this torque depends on the force of gravity multiplied by the moment arm. If the moment arm of the stand is extended in length in order to reach the body site to be treated, then the resultant torque force may be sufficient to displace the arm away from the site.

The need exists therefore for an adjustable stand anchored on a base to support a therapeutic heat applicator that is capable of placing the applicator at a properly oriented position adjacent a selected site on the body of a subject to be treated, and of maintaining the set position regardless of its location relative to the base.

SUMMARY OF INVENTION

In view of the foregoing, the main object of the invention is to provide an adjustable stand anchored on a base to support an electrically-powered therapeutic heat applicator adapted to place the applicator to which power is supplied through the stand at a properly-oriented position adjacent a selected site on the body of a subject to be treated, and of maintaining the set position regardless of its location relative to the base.

While an adjustable stand in accordance with the invention is especially useful in connection with a pulsed-heat applicator of the type disclosed in the above-identified Guibert patent, its use is by no means limited thereto, for the stand is capable of operating with other types of electrically-powered thermal, visible, light or radiant energy applicators.

More particularly, an object of this invention is to provide an adjustable stand of the above type which includes a series of arms in which at least two adjacent arms in the series are articulated by a knuckle which permits the arms to swing about axes at right angles to each other to permit a wide range of angular adjustment.

A significant feature of the invention is that the arms in the series thereof are tubular and the cable supplying power to the applicator passes through these arms whereby the cable is protectively concealed by the arms.

Briefly stated, these objects are attained by an adjustable stand anchored on a base to support an electrically-powered applicator so that it may be brought by an operator to a properly oriented position adjacent a selected site on the body of a subject to be treated and maintained at its set position.

The stand is composed of a series of interconnected arms, at least two adjacent arms being formed by pipes having a right angle bend and articulated by a knuckle formed by a four-sided rectangular block. The block has a first bore extending between one pair of opposing sides and a second bore extending between the other pair, an end of one arm being socketed in the first bore and the adjacent end of the other arm being socketed in the second bore whereby the arms articulated by the knuckle are swingable about axes at right angles to each other to afford a wide range of angular adjustment. Extending from each bore to a side related of the block is a slot which together with the bore and a set screw bridging the slot defines a friction clutch that engages the arm socketed in the bore to maintain its angular position.

BRIEF DESCRIPTION OF DRAWING

For a better understanding of the invention as well as other objects and further features thereof, reference is made to the following detailed description to be read in conjunction with the accompanying drawings, wherein:

FIG. 1 illustrates an adjustable stand in accordance with the invention;

FIG. 2 is a sectional view of the telescopic arm included in the stand;

FIG. 3 shows one side of the coupling block forming a knuckle articulating adjacent arms of the stand;

FIG. 4 shows another side of the coupling block;

FIG. 5 is a perspective view of the coupling block;

FIG. 6 shows a shim that is inserted in a slot in the block to engage a cut out in a pipe socketed therein; and FIG. 7 shows a knuckle provided with a ratchet bearing.

DESCRIPTION OF INVENTION

The Stand:

Referring now to FIGS. 1 and 2, shown in these figures is a pulse-heat applicator represented by block 10 and an adjustable stand therefor, generally identified by reference numeral 11. Stand 11 which is anchored on a base 12 is adapted to place applicator 10 at a properly oriented position adjacent a selected site on the body B of a subject to be treated by heat emanating from the applicator and to maintain the applicator at its set position.

In the case of an electrically-powered pulsed-heat applicator of the type disclosed in the above-identified Guibert patent, base 10 is provided with an electronic control unit which supplies power to the applicator through a cable running through stand 11. The applicator, in this instance, includes a motor-driven fan whose velocity is periodically changed to blow air through a heater coil, the electronic control unit supplying to this motor a voltage whose magnitude increases periodically in amplitude, thereby cause the fan to run alternately fast and slow to produce periodic high-temperature pulses.

Applicator 10 is supported on the free end of adjustable stand 11 which is constituted by a series of interconnected arms. The leading arm 13 in this series is formed by a pipe having a 90 degree bend so that the front end of its pipe is at right angles to the rear end. The front end of pipe 13 is plugged into a collar 14 projecting from applicator 10 so that the applicator can be rotated with respect to the pipe to assume any desired angle within predetermined limits. This angle is maintained by a half-dog point set screw 15 received in a threaded bore in collar 14 to engage an arcuate cut in the pipe end received therein to limit the degree to which applicator 10 is free to rotate.

The leading arm 13 of the adjustable stand is articulated to the next arm 17 in the series by a knuckle 16, arm 17 also being in the form of a pipe having a 90 degree bend. The structure of knuckle 16 is such that arm 13 is swingable with respect to the knuckle about one axis and arm 17 is swingable with respect to the knuckle about an axis at right angles to the one axis, thereby making possible a wide range of angular adjustment.

Arm 17 is joined to the end of a hollow piston rod 18 of a telescopic arm 19 of adjustable length which makes it possible to lengthen or shorten the adjustable stand. The other end of piston rod 18 is connected to a piston 20 slidable in cylinder 21 of the telescopic arm, whereby the length of the telescopic arm depends on the degree to which piston 20 is advanced within cylinder 21. Piston 20 is provided with a center bore in line with the hollow of the rod.

The other end of telescopic arm 19 is joined to an arm 22 which like arms 13 and 17 is formed by a pipe having a 90 degree bend. Arm 22 is articulated by a knuckle 23 to a straight arm 24 formed by an upright pipe which is anchored on base 12.

Thus arms 13, 17, 22 and 24 are all tubular pipes, and the telescopic arm 19 interconnecting arms 17 and 22 is hollow and therefore provides a passage communicating with these pipes. Hence it becomes possible to supply power from base 12 to applicator 10 by a cable 25 which runs through arms 24, 22, 19, 17 and 13. In cylinder 21 of telescopic arm 19, cable 25 is helically coiled to form a coil 25C that is stretched when the telescopic arm is lengthened.

The range of adjustment afforded by adjustable stand both with respect to length and angle is extensive. The telescopic arm 19 makes it possible to lengthen or shorten the stand, while the coupling between applicator 10 and the leading arm 13 of the stand 11 makes it possible to angle the applicator with respect to this arm. And by swinging arm 22 or knuckle 23 with respect to the base-anchored upright arm 24, one may lower or raise the applicator and cause it to assume a correct angle with respect to a body to be treated.

And leading arm 13 on which the applicator is supported, may be rotated on knuckle 16 about a first axis to cause the applicator to assume a desired angle with respect to this knuckle while arm 17 which is joined to telescopic arm 19 may be rotated about knuckle 16 about an axis at right angle to the first axis, making further angular adjustments possible.

Thus regardless of the location of the site on the body of a subject, the adjustable stand on which the applicator is supported can be brought to a properly-oriented position adjacent the site and maintained at its set position. The means by which the set position is maintained will now be described.

Knuckles:

Knuckles 16 and 23 have an identical structure; hence in describing these knuckles in FIGS. 3 to 6, we shall focus only on knuckle 16 which articulates bent pipe arms 13 and 17.

Knuckle 16 is formed of a rectangular block of high-strength synthetic plastic material, such as polypropylene, having four sides $S_1$ to $S_4$. A first socket bore $B_1$, adjacent the upper end of the block extends between the first pair of opposing sides $S_1$ and $S_2$. And a second socket bore $B_2$ adjacent the bottom end of the block extends between the second pair of opposing sides $S_3$ and $S_4$.

The diameter of the bores matches the outer diameter of bent pipe arms 13 and 17, the end of arm 13 being socketed in socket bore $B_1$ and the end of arm 17 being socketed in socket bore $B_2$.

Extending between bore $B_1$ and side $S_3$ of the block is a narrow slot $C_1$ which is in line with the longitudinal axis of the bore and defines in conjunction with the bore a friction clutch that engages the end of the arm 13 socketed in this bore. Extending between Bore $B_2$ and side $S_1$ of the block is a narrow slot $C_2$ which is in line with the longitudinal axis of that bore and defines in conjunction therewith a friction clutch that engages the end of arm 17 socketed in this bore.

Bridging slot $C_1$ is a set screw 26 having an enlarged head to facilitate turning the screw with the fingers. When tightened, screw $C_1$ reduces the gap between the walls of slot $C_1$ and thereby tightens the clutch. Bridging slot $C_2$ of the other friction clutch is a similar set screw 27.

When the set screws are loosened, arms 13 and 17 are then free to rotate in bores $B_1$ and $B_2$ in which they are socketed, and the adjustable stand may be manipulated to place the applicator at a properly oriented position adjacent a selected body site on the subject to be treated. And when the applicator is set to its operative position, the setting is maintained by the friction clutch or by tightening the set screws on the knuckles 16 and 23.

In order to limit the degree to which an arm may be rotated with respect to the knuckle to a useful angular range of about 220 degrees, the end of each arm, such as arm 13 shown in FIG. 6, is provided with an arcuate cut out 13A which defines the permissible limits of rotation.

Inserted in slot $C_1$ is a metal shim 28 whose thickness is less than the width of the gap so that it does not interfere with tightening the friction clutch. Shim 28 is provided with a hole 28h through which set screw 26 passes in bridging the slot, this shim being therefore held in place in slot $C_1$. Shim 28 is provided with a tongue 28 T that enters into the arcuate cut out 13A and therefore prevents arm 13 from rotating beyond the end limits of the arcuate cut out and holds the arm inside the knuckle.

It will be seen in FIGS. 3 and 4 that cable 25 supplying power to applicator 10 runs through pipe 17 into knuckle 16 from which it emerges to form a hoop 25h before entering pipe 13 in the knuckle leading to the applicator. External hoop 25h is never twisted more than about a half turn regardless of how the stand is adjusted.

Knuckle with Ratchet Bearing:

When the adjustable stand is very long, then the applicator supported thereby, as pointed out previously, may be subjected to torque forces which seek to displace it from its set position. If the friction clutch is tightened to prevent such displacement, then it becomes difficult to further adjust the position of the applicator so that it is properly oriented.

In the knuckle structure shown schematically in FIG. 7 socketed in bore $B_1$ and held therein by the friction clutch is a unidirectional ratchet bearing 29, and received in this bearing is the end of arm 22, so that the arm is rotatable in the bearing, not in the bore, and the bearing is rotatable in the bore.

A suitable commercially-available ratchet bearing for this purpose is the Torrington Company "drawn cup roller clutch" which transmits torque between a shaft and the bearing in one direction and allows free overrun in the opposite direction.

The unidirectional bearing 29 offers resistance through the friction clutch to turning arm 22 clockwise to lower applicator 10, but offers no resistance to the rotation of arm 22 counterclockwise to raise the applicator.

Hence when the applicator is brought down to occupy a desired position adjacent a selected site on the body of the subject it is then resistant to torque forces which seek to lower the applicator from its set position, but it is free to being raised by an operator from its set position. The use of a unidirectional bearing in a knuckle having a friction clutch is appropriate to adjustable stands which are relatively long and therefore subject the applicator supported thereby to a substantial moment of force.

While there has been shown a preferred embodiment of an adjustable stand for heat applicator in accordance with the invention, it will be appreciated that many changes may be made therein without departing from the spirit of the invention. Thus the telescopic arm 19 shown in FIG. 1 may be omitted in an adjustable stand that need not be capable of being lengthened.

We claim:

1. An adjustable stand anchored on a base to support an electrically-powered applicator so that it may be brought by an operator to a properly oriented position adjacent a selected site on the body of a subject to be treated and maintained at its set position, said stand comprising a series of interconnected arms, including a leading arm and a trailing arm, the leading arm in the series being joined to said applicator, the trailing arm in the series being anchored on the base, at least two adjacent arms in the series being articulated by a knuckle whereby these arms are swingable about axes at right angles to each other to afford a wide range of adjustment, said two adjacent arms being each formed by a pipe having a 90 degree bend.

2. A stand as set forth in claim 1, in which all arms in the series are hollow and in which power is supplied to the applicator by a cable which runs through the series of arms.

3. A stand as set forth in claim 1, in which one of said arms is a telescopic arm to permit the stand to be lengthened or shortened.

4. A stand as set forth in claim 3, in which the telescopic arm is composed of a tubular piston rod coupled to a piston having a bore therein slidable in a cylinder, the length of the arm depending on the degree to which the piston is advanced in the cylinder, power for the applicator being supplied by a cable which runs through the cylinder and via the bore in the piston through the tubular piston rod.

5. A stand as set forth in claim 4, in which power for the applicator is supplied by said cable that comes out of the pipe socketed in the first bore to form a hoop external to the block before going into the pipe socketed in the second bore.

6. A stand as set forth in claim 1, in which the knuckle is formed by a four-sided rectangular block having a first bore therein extending between one pair of opposing sides and a second bore therein extending between the other pair; an end of one pipe being socketed in the first bore and an end of the adjacent pipe being socketed in the second bore.

7. A stand as set forth in claim 6, in which the block is provided with a slot extending from the first bore to a related side of the block and a slot extending from the second bore to a related side of the block, each slot together with the bore and a set screw bridging the slot defining a friction clutch that engages the pipe socketed in the bore to maintain its angular position.

8. A stand as set forth in claim 7, in which the pipe socketed in the bore is provided with an arcuate cut out and inserted in the slot is a shim having a projecting tongue that is received in the cut out to limit the degree to which the pipe is rotatable and holds the pipe inside the knuckle.

9. A stand as set forth in claim 6, in which the pipe socketed in the first bore of the knuckle is received within a unidirectional ratchet bearing which frictionally resists a swing of the pipe with respect to the knuckle in one direction and freely permits a swing of the pipe in an opposite direction.

10. A stand as set forth in claim 1, in which the applicator is a pulsed heat applicator.

* * * * *